United States Patent [19]

Sanderson et al.

[11] Patent Number: 5,233,116

[45] Date of Patent: * Aug. 3, 1993

[54] PROCESS FOR PREPARING OLIGOMERS HAVING LOW UNSATURATION

[75] Inventors: John R. Sanderson, Leander; John F. Knifton; Edward T. Marquis, both of Austin, all of Tex.

[73] Assignee: Texaco Chemical Company, White Plains, N.Y.

[*] Notice: The portion of the term of this patent subsequent to Oct. 1, 2008 has been disclaimed.

[21] Appl. No.: 705,435

[22] Filed: May 24, 1991

[51] Int. Cl.$^5$ .................................................. C07C 2/08
[52] U.S. Cl. ....................................... 585/533; 585/18
[58] Field of Search .................. 585/533, 500, 502, 18

[56] References Cited

U.S. PATENT DOCUMENTS

| | | | |
|---|---|---|---|
| 2,951,087 | 8/1960 | Hauser et al. | 502/62 |
| 3,412,039 | 11/1968 | Miller | 502/81 |
| 3,432,571 | 3/1969 | Noddings et al. | 585/300 |
| 3,459,815 | 8/1969 | Noddings et al. | 568/896 |
| 3,845,150 | 10/1974 | Yan et al. | 208/135 |
| 3,849,507 | 11/1974 | Zuech | 585/455 |
| 4,153,638 | 5/1979 | Bercik et al. | 585/526 |
| 4,299,730 | 11/1981 | Sommer et al. | 252/435 |
| 4,351,980 | 9/1982 | Reusser et al. | 585/820 |
| 4,380,509 | 4/1983 | Sommer et al. | 252/453 |
| 4,456,779 | 6/1984 | Owen et al. | 585/415 |
| 4,480,142 | 10/1984 | Cobb | 585/465 |
| 4,531,054 | 7/1985 | Gregory et al. | 585/415 |
| 4,604,491 | 8/1986 | Dressler et al. | 585/26 |
| 4,808,559 | 2/1989 | Sommer et al. | 502/63 |
| 4,827,064 | 5/1989 | Wu | 585/10 |
| 4,879,425 | 11/1989 | Kukes et al. | 585/350 |
| 5,053,569 | 10/1991 | Marquis et al. | 585/255 |

FOREIGN PATENT DOCUMENTS 0759529 8/1980 U.S.S.R.
1489646 10/1977 United Kingdom.

OTHER PUBLICATIONS

Kuliev et al., "Preparation of High-Viscosity Synthetic Lubricants Using an Aluminosilicate Catalyst" Azer. Neft. Khoz., 1983, No. 4, pp. 40-43.

Chaudhuri and Sharma, "Some Novel Aspects of the Dimerization α-Methylstyrene with Acidic Ion-Exchange Resins, Clays, and Other Acidic Materials as Catalysts," Ind. Eng. Res., vol. 28, pp. 1757-1763 (1989).

Figueras, "Pillared Clays as Catalysts," *Catal. Rev.-Sci. Eng.*, 30(3), pp. 457-499 (1988).

Friedlander, "Organized Polymerization. I. Olefins on a Clay Surface," Journal of Polymer Science: Part C, No. 4, pp. 1291-1301.

Friedlander et al., "Organized Polymerization III. Monomers Intercalated in Montmorillonite," *Polymer Letters*, vol. 2, pp. 475-479 (1964).

"Intercalated Catalysts and Pillared Clays," from a Process Evaluation/Research Planning Report by (List continued on next page.)

*Primary Examiner*—Asok Pal
*Assistant Examiner*—P. Achutamurthy
*Attorney, Agent, or Firm*—Jack H. Park; Kenneth R. Priem; Russell R. Stolle

[57] ABSTRACT

Synthetic lubricant base stocks may be prepared in good yield by oligomerizing linear olefin monomers using certain acidic calcium montmorillonite clay catalysts. When the oligomers are prepared at a temperature greater than about 200° C., and any unreacted linear olefin monomer is removed, oligomers having an iodine value less than about 3 mg/g are obtained. An even lower iodine value is obtained when a hydrocarbon possessing a tertiary hydrogen is mixed with the linear olefin feed, and the mixture is contacted with the clay at a temperature greater than about 200° C. Little or no hydrogenation may be required of oligomers prepared in this manner to obtain base stocks suitable for use as synthetic lubricants.

20 Claims, No Drawings

OTHER PUBLICATIONS

Chem Systems, titled Catalysts: Selected Developments, pp. 239-249 (Dec. 1985).

Bolan, "synthetic Lubricant Base Stocks," Process Economics Program Report No. 125A by SRI International, Apr. 1989 & Supplemental A, Sep. 1989.

"Synthetic Lubricants from Internal Olefins," Process Evaluation/Research Planning Report by Chem Systems, 84-Q-1, pp. 17-45 year unknown.

Adams, "Synthetic Organic Chemistry Using Pillared, Cation-Exchanged and Acid-Treated Montmorillonite Catalysts—A Review", *Applied Clay Science*, 2 (1987) pp. 309-342.

Adams et al., "Clays as Selective Catalysts in Organic Synthesis," *Journal of Inclusion Phenomena*, vol. 5, (1987), pp. 663-674.

Purnell, "Catalysts by Ion-Exchanged Montmorillonites," *Catalysis Letters*, 5 (1990), pp. 203-210.

PROCESS FOR PREPARING OLIGOMERS HAVING LOW UNSATURATION

CROSS-REFERENCE TO RELATED APPLICATIONS

This application is related to the following co-pending U.S. patent applications: Ser. No. 07/500,631, filed Mar. 28, 1990, now U.S. Pat. No. 5,053,569, which relates to the preparation of synthetic lubricant base stocks by oligomerizing linear olefins by means of certain acidic montmorillonite clays; Ser. No. 07/516,931, filed Apr. 30, 1990, now U.S. Pat. No. 5,146,023, which relates to the preparation of synthetic lubricant base stocks by oligomerizing certain mixtures of internal and alpha-olefins by means of certain acidic montmorillonite clays; Ser. No. 07/516,870, filed Apr. 30, 1990, now U.S. Pat. No. 5,180,864, which relates to synthetic lubricant base stocks made by oligomerizing linear olefins by means of certain aluminum nitrate-treated acidic montmorillonite clays; Ser. No. 07/522,941, filed May 14, 1990, now U.S. Pat. No. 5,105,137, which relates to the preparation of synthetic lubricant base stocks by co-oligomerizing propylene and long-chain alpha-olefins by means of certain acidic montmorillonite clay catalysts; Ser. No. 07/525,807, filed May 21, 1990, now U.S. Pat. No. 5,030,971, which concerns synthetic lubricant base stocks made by co-oligomerizing 1,3-di-isopropenyl benzene and long-chain alpha-olefins by means of certain acidic montmorillonite clay catalysts; Ser. No. 07/531,172, filed May 31, 1990, now U.S. Pat. No. 5,171,904 which concerns synthetic lubricant base stocks having an improved pour point; Ser. No. 07/534,080, filed Jun. 6, 1990, now U.S. Pat. No. 5,169,550, which concerns synthetic lubricant base stocks having an improved viscosity; Ser. No. 07/536,906, filed Jun. 12, 1990, which concerns synthetic lubricant base stocks made by co-reacting olefins and anisole or like compounds; Ser. No. 07/545,260, filed Jun. 28, 1990, which concerns mixtures of oligomers and certain alkylated aromatics as synthetic lubricant base stocks; Ser. No. 07/551,969, filed Jul. 12, 1990, now U.S. Pat. No. 5,097,085, which concerns a process for oligomerizing olefins using phosphorous-containing acid on montmorillonite clay; Ser. No. 07/577,385, filed Aug. 31, 1990, now U.S. Pat. No. 5,171,909 which concerns synthetic lubricant base stocks prepared from long-chain vinylidene olefins and long-chain alpha and/or internal olefins; Ser. No. 07/580,439, filed Sep. 10, 1990, which concerns synthetic lubricant base stocks by co-reaction of vinylcyclohexene and long-chain olefins; Ser. No. 07/676,492, filed Mar. 28, 1991, now U.S. Pat. No. 5,180,866 which concerns a process for preparing synthetic lubricant base stocks having improved viscosity from vinylcyclohexene and long-chain olefins; and Ser. No. 07/699,533, filed May 14, 1991, now U.S. Pat. No. 5,180,869 which concerns a process for preparing high viscosity synthetic lubricant base stocks from a mixture of poly(isobutylene) and linear olefins. The totality of each of these previously filed applications is incorporated herein by reference.

BACKGROUND OF THE INVENTION

The invention relates to the preparation of synthetic lubricant base stocks. Synthetic lubricants are prepared from manmade base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt or higher are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium or high viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a nonhazardous, non-polluting catalyst would be a substantial improvement in the art.

Kuliev et al. attempted to prepare synthetic lubricants by oligomerizing long-chain ($C_9$-$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40-43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little aromatic by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $m^2/g$ or greater. In addition to being excellent catalysts, these clays are non-hazardous and nonpolluting.

With respect to the present invention, Applicants have found, surprisingly, that an oligomer bottoms product containing very little unsaturation may be obtained by oligomerizing the olefin feed at a temperature greater than about 200° C. Applicants also have discovered that a bottoms product having an even lower degree of unsaturation is obtained when a hydrocarbon possessing a tertiary hydrogen (a "tertiary hydrocarbon") is mixed with the linear olefin feed, and the mixture is contacted with the clay at a temperature greater than about 200° C. Little or no hydrogenation may be required of oligomers prepared in this manner to obtain base stocks suitable for use as synthetic lubricants.

SUMMARY OF THE INVENTION

The invention relates to a process for the preparation of oligomers having an iodine number less than about 3 mg/g, comprising
(1) contacting a linear olefin monomer containing from 10 to 24 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 $m^2/g$ or greater, wherein the olefin is contacted with the clay at a temperature greater than about 200° C., and
(2) removing any unreacted linear olefin monomer from the resulting oligomers. The invention further relates to a process for the preparation of oligomers having an iodine number less than about 1 mg/g, comprising
(1) contacting
   (a) a mixture of a tertiary hydrocarbon and a linear olefin monomer containing from 10 to 24 carbon atoms with
   (b) a catalytically effective amount of an acidic calcium montmorillonite clay having a moisture content ranging up to about 20 wt. %, a residual acidity in the range of about 3 to about 30 mg KOH/g, and a surface area of about 300 $m^2/g$ or greater, wherein the mixture is contacted with the clay at a temperature greater than about 200° C., and
(2) removing any unreacted linear olefin monomer and unreacted tertiary hydrocarbon from the resulting oligomers. The invention also relates to a process for the preparation of oligomers having an iodine number less than about 1 mg/g, comprising
(1) contacting
   (a) a mixture of methylcyclopentane and a linear olefin monomer containing from 10 to 24 carbon atoms with
   (b) a catalytically effective amount of an acidic calcium montmorillonite clay having a moisture content ranging up to about 20 wt. %, a residual acidity in the range of about 3 to about 30 mg KOH/g, and a surface area of about 300 $m^2/g$ or greater, wherein the mixture is contacted with the clay at a temperature greater than about 200° C., and
(2) removing any unreacted linear olefin monomer and unreacted methylcyclopentane from the resulting oligomers.

DESCRIPTION OF THE PREFERRED EMBODIMENTS

Applicants discovered that synthetic lubricant base stocks may be prepared in high yield by oligomerizing long-chain linear olefins using certain acidic montmorillonite clay catalysts. Applicants have now discovered that an oligomer bottoms product containing very little unsaturation (iodine numbers less than 3 mg/g are observed) may be obtained by oligomerizing the olefin feed at a temperature greater than about 200° C. Optionally, a tertiary hydrocarbon may be added to the olefin monomer feed to further lower the unsaturation present in the bottoms product of the oligomerization reaction (to iodine numbers less than about 0.5 mg/g.)

Tertiary hydrocarbons—defined as hydrocarbons possessing a tertiary hydrogen—useful in the present invention include such compounds as methylcyclopentane, methylcyclohexane, methylcyclobutane, and the like. While many hydrocarbons that contain a tertiary hydrogen may be useful, methylcyclopentane is preferred. Preferably, the mixture of linear olefin monomer and tertiary hydrocarbon contains from about 5 to about 25 wt. % tertiary hydrocarbon. It is more preferred that the mixture of linear olefin monomer and tertiary hydrocarbon contain from about 10 to about 15 wt.% tertiary hydrocarbon.

The olefin monomer feed stocks used in the present invention may be selected from compounds comprising (1) alpha-olefins having the formula $R''CH=CH_2$, where R″ is an alkyl radical of 8 to 22 carbon atoms, and (2) internal olefins having the formula RCH═CHR′, where R and R′ are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 14 to 18, inclusive, with an especially preferred range being 14 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization of the linear olefin may be represented by the following general equation:

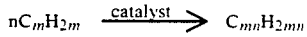

where n represents moles of monomer and m represents the number of carbon atoms in the monomer. Thus, the oligomerization of 1-decene may be represented as follows:

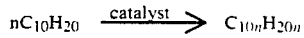

reaction occurs sequentially. Initially, olefin monomer reacts with olefin monomer to form dimers. Some of the dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Temporarily, each resulting oligomer contains one double bond. However, at the higher temperatures of the present invention, alkylation or cyclization occurs at most of the double bonds, eliminating much of the unsaturation that would otherwise be present in the bottoms product. When a tertiary hydrocarbon is included in the feed, the tertiary hydrocarbon readily participates in the alkylation, further decreasing the unsaturation that would otherwise be present in the bottoms product.

The catalysts used to effect this reaction in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

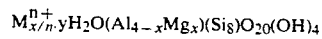

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants have discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 m$^2$/g or greater. Illustrative examples include Filtrol grade 24, having a moisture content of 12 wt. %, a residual acidity of 8.5 mg KOH/g, and a surface area of 425 m$^2$/g; Filtrol grade 124, having a moisture content of 2 wt. %, a residual acidity of 7.0 mg KOH/g, and a surface area of 400 m$^2$/g; Filtrol grade 13, having a moisture content of 16 wt. %, a residual acidity of 15 mg KOH/g, and a surface area of 300 m$^2$/g; Filtrol grade 113, having a moisture content of 4 wt. %, a residual acidity of 10 mg KOH/g, and a surface area of 300 m$^2$/g; and Filtrol grade 224, having virtually no moisture, and having a residual acidity of 3.0 mg KOH/g, and a surface area of 350 m$^2$/g.

Preferably, the catalyst is activated by heat treatment before running the reaction. Applicants have found, surprisingly, that heat treatment of the catalyst prior to running the oligomerization reaction causes the catalyst to be more active and produce a higher olefin conversion. Additionally, clays heat treated in this manner are more stable, remaining active during the oligomerization reaction for a longer period of time. The clays may be heat treated at temperatures in the range of about 50° to 400° C., with or without the use of a vacuum. A more preferred temperature range is 50° to 300° C. Optionally, an inert gas may be used during heat treatment as well. Preferably, the clay should be heat treated under conditions and for a length of time which will reduce the water content of the clay to approximately 1 wt. % or less.

The oligomerization reaction may be carried out in either a stirred slurry reactor or in a fixed bed continuous flow reactor. The catalyst concentration should be sufficient to provide the desired catalytic effect. To obtain the surprising improvement in unsaturation obtained using the present invention, the oligomerization may be performed at a temperature between about 200° and 300° C., with the preferred range being greater than about 220° C. It is more preferred that the reaction by performed at a temperature greater than about 240° C. The reaction may be run at pressures of from 0 to 1000 psig.

While a object of the present invention is to substantially reduce or eliminate the need for a hydrogenation procedure following the oligomerization reaction, for some applications a hydrogenation step, albeit less strenuous and consuming less hydrogen than would otherwise be necessary, may be advantageous. Thus, any unsaturation still remaining in the oligomers may be hydrogenated to further improve the thermal stability of the oligomers and to further guard against oxidative degradation during their use as lubricants. The hydrogenation reaction for 1-decene oligomers may be represented as follows:

$$C_{10n}H_{20n} + H_2 \xrightarrow{catalyst} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

While it is known to include a distillation step after the hydrogenation procedure to obtain products of various 100° C. viscosities, it is preferred in the method of the present invention that no further distillation (beyond monomer flashing) be conducted. In other words, the monomer-stripped (and, if desired, hydrogenated) bottoms ar the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The monomer stripping step should be conducted under mild conditions Distillation at temperatures exceeding 250° C. may cause the oligomers to break down in some fashion and come off as volaties. Preferably, therefore, the reboiler or pot temperature should be kept at or under about 225° C. when stripping out the monomer.

EXAMPLES

The following demonstrates the use of the present invention in batch reaction systems:

Batch-Flask $C_{14}$ alpha-olefin (200 g) and Harshaw/Filtrol Clay-13 catalyst were charged to a flask equipped with a stirrer, thermometer, heating mantle, and a water-cooled condenser ($N_2$ purge). The mixture was vigorously stirred and heated to the desired temperature for the desired time. The mixture was then cooled to ambient temperature and filtered with suction. The liquid effluent was analyzed by liquid chromatography. The unreacted monomer was then removed under vacuum, and the iodine number (measured of unsaturation) determined on the bottoms product. The results are detailed in the following table.

| Ex. No. | Wt. of $C_{14}$ Olefin (g) | Wt. of Clay-13 Catalyst (g) | Time/ Temp (Hr/°C.) | Con. (%) | D/T+ | Bottoms $I^2$ No. |
|---|---|---|---|---|---|---|
| 1 | 200 | 20 | 6/140 | 78.3 | 1.30 | 4.66 |
| 2 | 200 | 20 | 5/160 | 85.0 | 1.31 | 4.43 |
| 3 | 200 | 20 | 4/180 | 85.6 | 1.12 | 3.81 |
| 4 | 200 | 20 | 2/200 | 80.7 | 1.59 | 2.74 |
| 5 | 200 | 10 | 6/140 | 61.1 | 1.57 | 4.39 |
| 6 | 200 | 30 | 6/140 | 80.7 | 1.27 | 4.36 |
| 7 | 200 | 20 | 2/220 | 79.6 | 2.4 | 0.90 |
| 8 | 200 | 20 | 2/240 | 75.1 | 2.29 | 0.70 |
| 9 | 200 | 20 | 2/200 | 84.2 | 1.01 | 3.62 |
| 10 | 200 | 20 | 4/200 | 80.9 | 1.71 | 1.53 |
| 11 | 200 | 20 | 6/200 | 77.0 | 1.81 | 0.66 |

Con. = Conversion; D = Dimer; T+ = Trimer + Tetramer + higher oligomers.

Batch-Autoclave

Liquid reactants and Harshaw/Filtrol Clay-13 catalyst were charged to an autoclave and the autoclave was sealed. The mixture was vigorously stirred and heated to the desired temperature for the desired time. The mixture was then cooled to ambient temperature and filtered with suction. The liquid effluent was analyzed by liquid chromatography. The unreacted monomer was then removed under vacuum, and the iodine number (measure of unsaturation) determined on the bottoms product. The results are detailed in the following table.

| Ex. No. | Wt. of $C_{14}$ Olefin (g) | Alkane | Wt. of Alkane (g) | Wt. of Clay-13 Catalyst (g) | Time/ Temp (Hr/°C.) | Con. (%) | M (%) | D (%) | T+ (%) | D/T+ | Bottoms $I^2$ No. |
|---|---|---|---|---|---|---|---|---|---|---|---|
| 1 | 260 | MCP | 40 | 30 | 4/160 | 78.8 | 21.2 | 51.1 | 27.7 | 1.84 | 7.33 |
| 2 | 260 | MCP | 40 | 30 | 4/180 | 88.2 | 11.2 | 48.7 | 35.4 | 1.38 | 3.97 |
| 3 | 260 | MCP | 40 | 30 | 4/200 | 86.6 | 13.4 | 46.2 | 30.1 | 1.53 | 0.08 |
| 4 | 260 | MCP | 40 | 30 | 4/250 | 74.5 | 25.5 | 47.2 | 11.4 | 4.14 | 0.08 |
| 5 | 300 | MCP | 40 | 30 | 5/160 | 79.5 | 20.5 | 49.5 | 26.9 | 1.84 | 9.25 |
| 6 | 300 | MCP | 20 | 30 | 5/160 | 76.6 | 23.4 | 46.3 | 28.8 | 1.61 | 8.10 |
| 7 | 300 | None | 0 | 30 | 5/160 | 81.7 | 18.3 | 44.4 | 33.5 | 1.33 | 7.77 |
| 8 | 320 | MCH | 80 | 40 | 5/160 | 83.0 | 17.0 | 40.6 | 34.4 | 1.18 | 3.85 |
| 9 | 320 | MCH | 80 | 40 | 5/180 | 88.8 | 11.2 | 44.5 | 37.2 | 1.20 | 3.83 |
| 10 | 320 | 2-MB | 80 | 40 | 5/160 | 84.4 | 15.2 | 47.5 | 37.2 | 1.28 | 8.34 |
| 11 | 320 | 2-MB | 80 | 40 | 5/180 | 88.9 | 11.1 | 50.8 | 38.1 | 8.29 | 8.29 |

MCP = Methylcyclopentane; MCH = Methylcyclohexane; 2-MB = Methylcyclobutane; Con. = Conversion; D = Dimer; T+ = Trimer + tetramer + higher oligomers.

The invention will be further illustrated by the following examples, which are given by way of illustration and not as limitations on the scope of this invention.

We claim:

1. A process for the preparation of oligomers having an iodine number less than about 3 mg/g, comprising (1) contacting a linear olefin monomer containing from 10 to 24 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 m$^2$/g or greater, wherein the olefin is contacted with the clay at a temperature of about 200° C. to about 300° C. and (2) removing any unreacted linear olefin monomer from the resulting oligomers.

2. The process of claim 1, wherein the moisture content of the acidic calcium montmorillonite clay is about 12 wt. %, the residual acidity is about 8.5 mg KOH/g, and the surface area is about 425 m$^2$/g.

3. The process of claim 1, wherein the moisture content of the acidic calcium montmorillonite clay is about 2 wt. %, the residual acidity is about 7.0 mg KOH/g, and the surface area is about 400 m$^2$/g.

4. The process of claim 1, wherein the moisture content of the acidic calcium montmorillonite clay is about 16 wt. %, the residual acidity is about 15 mg KOH/g, and the surface area is about 300 m$^2$/g.

5. The process of claim 1, wherein the moisture content of the acidic calcium montmorillonite clay is about 4 wt. %, the residual acidity is about 10 mg KOH/g, and the surface area is about 300 m$^2$/g.

6. The process of claim 1, wherein the moisture content of the acidic calcium montmorillonite clay is essentially nil, the residual acidity is about 3.0 mg KOH/g, and the surface area is about 350 m$^2$/g.

7. The process of claim 1, wherein the linear olefin monomer is mixed with a tertiary hydrocarbon prior to contact with the acidic calcium montmorillonite clay.

8. The process of claim 1, wherein the linear olefin monomer is contacted with the clay at a temperature of about 220° C. to about 300° C.

9. The process of claim 1, wherein the linear olefin monomer is contacted with the clay at a temperature of about 240° C. to about 300° C.

10. A process for the preparation of oligomers having an iodine number less than about 1 mg/g, comprising (1) contacting
  (a) a mixture of a tertiary hydrocarbon and a linear olefin monomer containing from 10 to 24 carbon atoms, wherein up to about 25 wt. % of the mixture is tertiary hydrocarbon, with
  (b) a catalytically effective amount of an acidic calcium montmorillonite clay having a moisture content ranging up to about 20 wt. %, a residual acidity in the range of about 3 to about 30 mg KOH/g, and a surface area of about 300 m$^2$/g or greater, wherein the mixture is contacted with the clay at a temperature of about 200° C. to about 300° C., and (2) removing any unreacted linear olefin monomer and unreacted tertiary hydrocarbon from the resulting oligomers.

11. The process of claim 10, wherein the moisture content of the acidic calcium montmorillonite clay is about 12 wt. %, the residual acidity is about 8.5 mg KOH/g, and the surface area is about 425 m$^2$/g.

12. The process of claim 10, wherein the moisture content of the acidic calcium montmorillonite clay is about 2 wt. %, the residual acidity is about 7.0 mg KOH/g, and the surface area is about 400 m$^2$/g.

13. The process of claim 10, wherein the moisture content of the acidic calcium montmorillonite clay is about 16 wt. %, the residual acidity is about 15 mg KOH/g, and the surface area is about 300 m$^2$/g.

14. The process of claim 10, wherein the moisture content of the acidic calcium montmorillonite clay is about 4 wt. %, the residual acidity is about 10 mg KOH/g, and the surface area is about 300 m$^2$/g.

15. The process of claim 10, wherein the moisture content of the acidic calcium montmorillonite clay is essentially nil, the residual acidity is about 3.0 mg KOH/g, and the surface area is about 350 m$^2$/g.

16. The process of claim 10, wherein, the mixture is contacted with the clay at a temperature of about 220° C. to about 300° C.

17. The process of claim 10, wherein the mixture is contacted with the clay at a temperature of about 240° C. to about 300° C.

18. The process of claim 10, wherein the tertiary hydrocarbon is methylcyclopentane.

19. A process for the preparation of oligomers having an iodine number less than about 1 mg/g, comprising (1) contacting
  (a) a mixture of methylcyclopentane and a linear olefin monomer containing from 10 to 24 carbon atoms, wherein up to about 25 wt. % of the mixture is tertiary hydrocarbon, with
  (b) a catalytically effective amount of an acidic calcium montmorillonite clay having a moisture content ranging up to about 20 wt. %, a residual acidity in the range of about 3 to about 30 mg KOH/g, and a surface area of about 300 m$^2$/g or greater, wherein the mixture is contacted with the clay at a temperature of about 200° C. to about 300° C., and (2) removing any unreacted linear olefin monomer and unreacted methylcyclopentane from the resulting oligomers.

20. The process of claim 19, wherein the resulting oligomers have an iodine value less than about 0.5 mg/g.

* * * * *